(12) United States Patent
Johansson et al.

(10) Patent No.: US 10,390,917 B2
(45) Date of Patent: Aug. 27, 2019

(54) POWERED ORAL CARE IMPLEMENT

(71) Applicant: COLGATE-PALMOLIVE COMPANY, New York, NY (US)

(72) Inventors: Patrik Johansson, Hoboken, NJ (US); Guofeng Xu, Plainsboro, NJ (US); Gerald Gontarz, Spotswood, NJ (US); Robert Moskovich, East Brunswick, NJ (US); Daniel Wainless, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 556 days.

(21) Appl. No.: 14/977,151

(22) Filed: Dec. 21, 2015

(65) Prior Publication Data
US 2016/0184065 A1 Jun. 30, 2016

Related U.S. Application Data

(60) Provisional application No. 62/096,574, filed on Dec. 24, 2014.

(51) Int. Cl.
*A46B 15/00* (2006.01)
*A61C 17/32* (2006.01)
(Continued)

(52) U.S. Cl.
CPC ............ *A61C 17/22* (2013.01); *A46B 11/002* (2013.01); *A46B 11/0003* (2013.01);
(Continued)

(58) Field of Classification Search
CPC ..... A61C 17/22; A61C 17/32; A46B 15/0022; A46B 15/0024; A46B 15/0026
See application file for complete search history.

(56) References Cited

U.S. PATENT DOCUMENTS 7,886,398 B2  2/2011 Morita et al.
8,595,882 B2  12/2013 Bax et al.
(Continued)

FOREIGN PATENT DOCUMENTS

CN      200953928          10/2007
DE   10 2005 009 958 A1 *  1/2007
(Continued)

OTHER PUBLICATIONS

International Search Report and Written Opinion mailed in International Application No. PCT/US2015/067121 dated Jun. 24, 2016.

*Primary Examiner* — Randall E Chin

(57) ABSTRACT

A powered toothbrush includes a handle, a power source disposed in the handle, a head including a cavity disposed at a distal end of the handle, an electrically conducting element disposed in the cavity and electrically connected to the power source, and a movable cleaning element connected to the head and movable relative to the cavity. The movable cleaning element includes a tooth cleaning support member, a tooth cleaning element mounted on the support member, and a ferromagnetic member. Application of an electrical current to the electrically conducting element generates a magnetic field at the electrically conducting element. The magnetic field selectively at least one of attracts and repels the ferromagnetic member to move the movable cleaning element relative to the electrically conducting element.

12 Claims, 5 Drawing Sheets

(51) Int. Cl.
*A61C 17/22* (2006.01)
*A46B 11/00* (2006.01)
*A61C 17/34* (2006.01)
*C25B 1/00* (2006.01)
*C25B 1/26* (2006.01)
*C25B 9/06* (2006.01)

(52) U.S. Cl.
CPC ...... *A46B 15/0002* (2013.01); *A46B 15/0022* (2013.01); *A46B 15/0024* (2013.01); *A46B 15/0026* (2013.01); *A61C 17/32* (2013.01); *A61C 17/3481* (2013.01); *C25B 1/00* (2013.01); *C25B 1/26* (2013.01); *C25B 9/06* (2013.01); *A46B 2200/1066* (2013.01)

(56) References Cited

U.S. PATENT DOCUMENTS

| | | |
|---|---|---|
| 8,668,397 B2 | 3/2014 | Barkhordar |
| 9,125,484 B2 | 9/2015 | Gatzemeyer |
| 2007/0071541 A1 | 3/2007 | Vila |
| 2014/0245553 A1* | 9/2014 | Gravina .................. A46B 9/04 15/167.1 |

FOREIGN PATENT DOCUMENTS

| | | |
|---|---|---|
| JP | 2009-045202 A | 3/2009 |
| WO | WO 2009/066647 | 5/2009 |
| WO | WO2009066647 | 5/2009 |
| WO | WO 2009/148442 | 12/2009 |
| WO | WO 2013/141359 | 9/2013 |

* cited by examiner

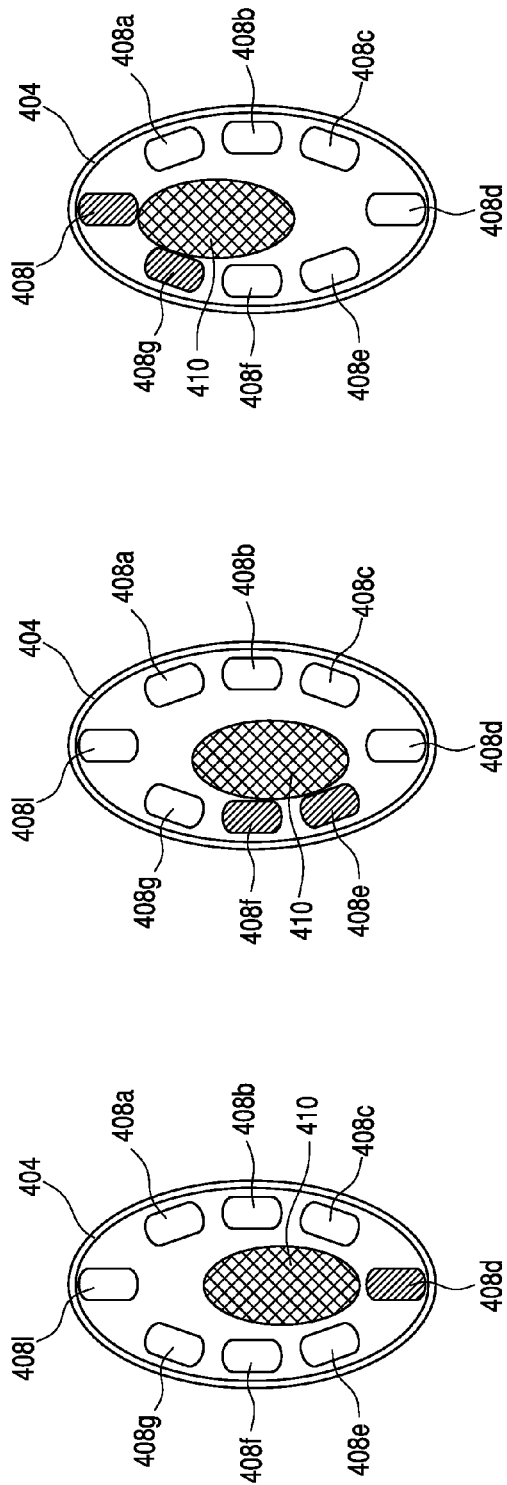
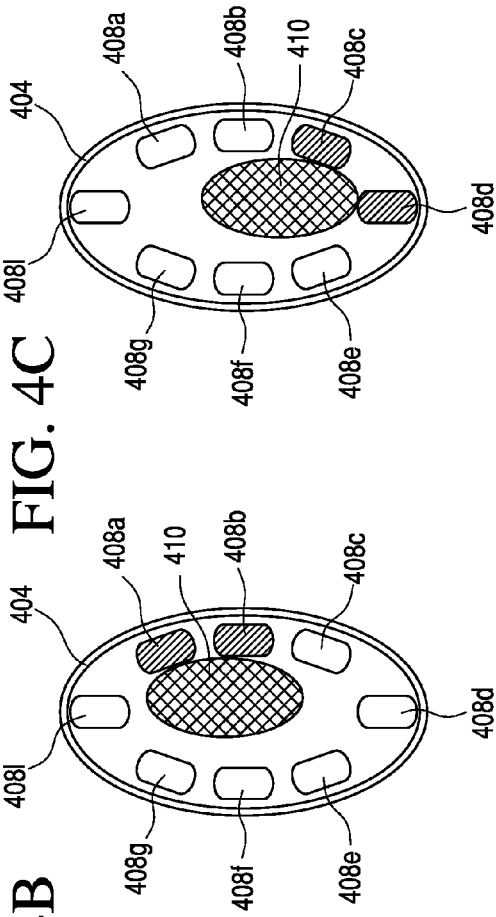
FIG. 4B
FIG. 4C
FIG. 4D
FIG. 4E
FIG. 4F

POWERED ORAL CARE IMPLEMENT

CROSS-REFERENCE TO RELATED APPLICATIONS

This application claims the priority benefit under 35 U.S.C. § 119(e) of U.S. Provisional Patent Application No. 62/096,574, filed Dec. 24, 2014, the entirety of which is hereby incorporated by reference.

BACKGROUND

Various powered oral care implements, such as powered toothbrushes, are conventionally known. Several such conventional toothbrushes house a motor or other actuator in the handle and transmit movement generated by the motor to a cleaning element at a head of the toothbrush. One conventional method for transmitting motion generated by the motor is via a driveshaft extending from the handle, through a neck of the toothbrush, to the cleaning element at the head. In these conventional devices, the brushing pattern is often limited by the design of the driveshaft. Moreover, in conventional toothbrushes of this sort, the electronics are contained completely within the handle, relatively far from the oral cavity.

Accordingly, there is a need in the art for an oral care implement in which the tooth cleaning elements are directly driven at the head of the implement.

Moreover, there is a need in the art for an oral care implement that can provide an electrical field in the head of the toothbrush, which may be used to promote oral health from within the oral cavity.

BRIEF SUMMARY

In aspects of this disclosure, a powered toothbrush includes a handle, a power source, a head including a cavity disposed at a distal end of the handle, an electrically conducting element disposed in the cavity and electrically connected to the power source, and a movable cleaning element connected to the head and movable relative to the cavity. The movable cleaning element includes a bristle support member disposed at least partially over the cavity, a plurality of bristles extending from the bristle support in a direction away from the cavity, and a ferromagnetic member. Application of an electrical current to the electrically conducting element generates a magnetic field at the electrically conducting element. The magnetic field selectively at least one of attracts and repels the ferromagnetic member to move the movable cleaning element relative to the electrically conducting element.

In one or more additional aspects, in a toothbrush as described in the preceding paragraph, the electrically conducting element comprises an electrode.

In one or more additional aspects, in a toothbrush as described in any of the preceding paragraphs, the electrically conducting element comprises an electrical coil disposed about a ferromagnetic member.

In one or more additional aspects, in a toothbrush as described in any of the preceding paragraphs, the bristle support member and the cavity define a volume and one or more of the electrically conducting element and the ferromagnetic member are disposed in the volume.

In one or more additional aspects, in a toothbrush as described in the preceding paragraph, a channel may extend between the volume and an exterior of the head.

In one or more additional aspects, in a toothbrush as described in any of the preceding paragraphs, a dentifrice slurry may be provided in the cavity.

In an additional aspect of this disclosure, a powered oral care implement includes a housing including a cavity, one or more electrically conducting elements disposed in the cavity, a power source electrically connected to each of the one or more electrodes, and a cleaning element disposed on the head to at least partially cover the cavity. Applying a current to individual of the one or more electrically conducting elements generates a field at the individual of the electrically conducting elements.

In one or more additional aspects, in an oral care implement as described in the preceding paragraph, the field at the individual of the electrically conducting elements is a magnetic field, and a ferromagnetic member is at least one of selectively attracted to and repelled by the magnetic field.

In one or more additional aspects, in an oral care implement as described in the preceding paragraph, the ferromagnetic member is fixed to the cleaning element and the cleaning element is configured to move relative to the one or more electrically conducting elements.

In one or more additional aspects, in an oral care implement as described in any of the preceding paragraphs, a dentifrice slurry is provided in the cavity.

In one or more additional aspects, in an oral care implement as described in the preceding paragraph, the one or more electrically conducting elements comprise one or more electrodes and the dentifrice slurry comprises one or more precursors converted by the electrodes to active species.

In one or more additional aspects, in an oral care implement as described in the preceding paragraph, the active species include at least one of a whitening agent, an enamel modifier, a mal-odor inhibitor, or an anti-bacterial.

In one or more additional aspects, in an oral care implement as described in the preceding paragraph, the cleaning element is movable relative to the cavity, the movable cleaning element and the cavity define a volume, and the movement of the movable cleaning element varies the volume.

In one or more additional aspects, in an oral care implement as described in the preceding paragraph, a channel fluidly connects the volume with an exterior of the head, and varying the volume causes selective ingress and egress of material into and out of the volume through the channel.

In one or more additional aspects, in an oral care implement as described in any of the preceding paragraphs, a valve regulates the ingress and egress of material into and out of the volume through the channel.

In one or more additional aspects, in an oral care implement as described in any of the preceding paragraphs, the channel extends between the volume and an opening in the movable cleaning element.

In one or more additional aspects, in an oral care implement as described in any of the preceding paragraphs, at least one of the one or more electrically conducting elements comprises a coil disposed around a ferrite core.

In one or more additional aspects, in an oral care implement as described in any of the preceding paragraphs, the one or more electrically conducting elements comprise a plurality of electrically conducting elements spaced about a periphery of the cavity.

In one or more additional aspects, in an oral care implement as described in any of the preceding paragraphs, the ferromagnetic member is movable along a plane extending between magnetic fields of the plurality of electrically conducting elements.

In one or more additional aspects, in an oral care implement as described in any of the preceding paragraphs, a controller may selectively apply the current to individual of the electrically conducting elements.

In another aspect of this disclosure, a method of treating an oral cavity providing a powered oral care implement comprising a head including a cavity, a cleaning element disposed to at least partially cover the cavity, and an electrically conducting element disposed in the cavity; and applying a current to the electrically conducting element to at least one of (1) impart a motion on the implement and (2) generate active oxygen species and/or therapeutic molecules.

In one or more additional aspects, in a method as described in the preceding paragraph, the cleaning element includes a ferromagnetic material, applying the current to the electrically conducting element moves the ferromagnetic member, and the movement of the ferromagnetic member varies a volume defined by the cavity and the cleaning element.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 4B-4F are schematic illustrations of an example method of operating the toothbrush illustrated in FIG. 4A;

DETAILED DESCRIPTION

This description of presently preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

This disclosure relates generally to powered oral care implements, and more particularly to powered implements, such as powered toothbrushes, with electrical components in a head of the implement. The following detailed description may generally refer to embodiments of the inventive powered implements in the context of a toothbrush, but the disclosure is not limited to toothbrushes; other oral care implements may also incorporate features of this disclosure. By way of non-limiting example, mouth guard-type oral care implements, which do not include a handle, are known, and aspects of this disclosure may be incorporated into such an implement.

Figure 1:
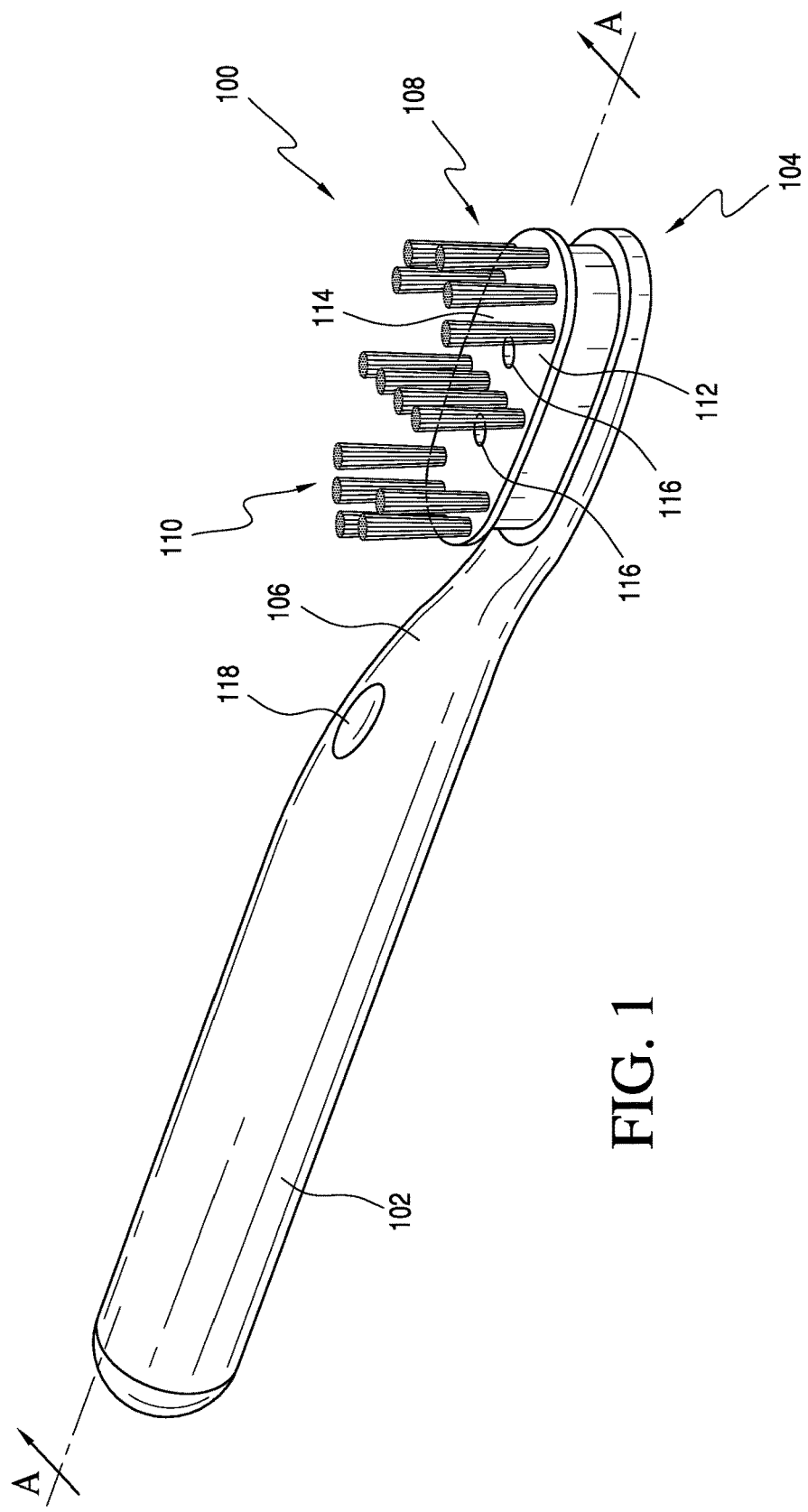
FIG. 1 is a perspective view of an oral care implement, embodied as a toothbrush, according to an example implementation of this disclosure.

FIG. 1 illustrates a toothbrush 100 according to a first implementation of this disclosure. The toothbrush 100 generally includes a handle 102, a head 104 disposed at the distal end of the handle 102, and a neck portion 106 generally disposed between the handle 102 and the head 104. As illustrated, the handle has a generally elongate shape, along a longitudinal axis. This disclosure is not limited to the shape and/or size of the toothbrush 100 illustrated in FIG. 1. In alternative implementations, one or more of the handle 102, head 104, and/or neck 106 may have different shapes, sizes, orientations, and/or the like. Additional features may also be incorporated into the toothbrush or disposed on the toothbrush.

In the embodiment illustrated in FIG. 1, the toothbrush 100 also includes a movable cleaning element 108 disposed on the head 104 to move relative to the head. The movable cleaning element 108 generally includes one or more tooth cleaning elements 110 disposed on a tooth cleaning element support 112. As used herein, the term "tooth cleaning elements" includes any type of structure that is commonly used or is suitable for use in providing oral health benefits (e.g., tooth cleaning, tooth polishing, tooth whitening, massaging, stimulating, etc.) by making intimate contact with portions of the teeth and/or gums. Such tooth cleaning elements include but are not limited to tufts of bristles that can be formed to have a number of different shapes and sizes, massage elements, and elastomeric cleaning members that can be formed to have a number of different shapes and sizes, or a combination of both tufts of bristles and elastomeric cleaning members. The tooth cleaning elements 110 may be arranged on the tooth cleaning element support 112 in many configurations.

In FIG. 1, the tooth cleaning elements 110 include bristles, which may be formed as bristle tufts. The tufts may be formed with bristles of the same or different bristle materials (such as nylon bristles, spiral bristles, rubber bristles, etc.). Moreover, while the tooth cleaning elements 110 may be arranged so that they are generally perpendicular to a top surface 114 of the tooth cleaning element support 112, some or all of the tooth cleaning elements may be angled at various angles with respect to the top surface 114. When the top surface 114 includes bristle tufts, it is thereby possible to select the combination of bristle configurations, bristle materials and/or bristle orientations to achieve specific intended results and operational characteristics, thus maximizing and enhancing cleaning, tooth polishing, tooth whitening, massaging, stimulation, and the like.

The tooth cleaning elements 110 may be attached to the tooth cleaning element support 112 by any conventional method. In certain embodiments, the tooth cleaning element support 112 may comprise a head plate having a plurality of holes formed there through, and the tooth cleaning elements may be mounted to the head plate within the holes. This type of technique for mounting the tooth cleaning elements to a head plate as the tooth cleaning element support 112 is generally known as anchor free tufting (AFT). In AFT a head plate or membrane is created and the tooth cleaning elements (such as bristles, elastomeric elements, and combinations thereof) are positioned into the head plate so as to extend through the holes of the head plate. The free ends of the tooth cleaning elements on one side of the head plate perform the cleaning function. The ends of the tooth cleaning elements on the other side of the head plate are melted together by heat to be anchored in place. As the tooth cleaning elements are melted together, a melt matte is formed, which is a layer of plastic formed from the collective ends of the tooth cleaning elements that connects the tooth cleaning elements to one another on one side of the head plate and prevents the tooth cleaning elements from being pulled through the tuft holes.

In some conventional designs, such as some conventional manual toothbrushes, after the tooth cleaning elements are secured to the head plate, the head plate may be secured to the head 104, such as by ultrasonic welding. When the head plate is coupled to the head 104, the melt matte is located between a lower surface of the head plate and a floor of a basin or cavity of the head 104 in which the head plate is disposed. The melt matte, which is coupled directly to and in fact forms a part of the tooth cleaning elements, prevents the tooth cleaning elements from being pulled through the holes in the head plate thus ensuring that the tooth cleaning elements remain attached to the head plate during use of the oral care implement.

In the illustrated embodiment, however, the head plate is not fixed to the head 104. Instead, the head plate comprises a portion of the movable cleaning element 108 disposed to move relative to the remainder of the head 104, neck 106, and handle 102.

In another embodiment, the tooth cleaning elements may be connected to a head plate or membrane later incorporated into the moveable cleaning element 108 using a technique known in the art as AMR. In this technique, a head plate is provided and the bristles are inserted into holes in the head plate so that free/cleaning ends of the bristles extend from the front surface of the head plate and bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some conventional applications, after formation of the melt matte, a tissue cleaner is injection molded onto the rear surface of the head plate, thereby trapping the melt matte between the tissue cleaner and the rear surface of the head plate. Other structures may be coupled to the rear surface of the head plate to trap the melt matte between the rear surface of the head plate and such structure without the structure necessarily being a tissue cleaner. For example, in embodiments of this disclosure, a structure covering the melt matte may be a plastic material that is used to form a smooth rear surface of the head, or the like. In still other embodiments, the structure can be molded onto the rear surface of the head plate or snap-fit (or other mechanical coupling) to the rear surface of the head plate as desired.

Of course, techniques other than AFT and AMR can be used for mounting tooth cleaning elements to the tooth cleaning element support 112, such as widely known and used stapling/anchoring techniques or the like. In such embodiments the tooth cleaning elements may be coupled directly to the tooth cleaning element support 112. Furthermore, in a modified version of the AFT process discussed above, the head plate may be formed by positioning the tooth cleaning elements within a mold, and then molding the head plate around the tooth cleaning elements via an injection molding process. However, it should be appreciated that certain of the bristle tufts disclosed herein may not be adequately secured to the head using staple techniques, and one of AFT or AMR may therefore be preferred for securing such bristle tufts to the support 112.

Moreover, in certain embodiments, the invention can be practiced with various combinations of stapled, IMT, AMR, or AFT cleaning elements. Alternatively, the tooth cleaning elements could be mounted to tuft blocks or sections by extending through suitable openings in the tuft blocks so that the base of the tooth cleaning elements is mounted within or below the tuft block. In still other embodiments, likely in which the tooth cleaning elements are not bristles, the tooth cleaning elements may be molded integrally with the tooth cleaning element support 112.

A plurality of apertures 116 is also illustrated in FIG. 1. The apertures 116 are disposed through the tooth cleaning element support 112 and provide a channel or passageway through the tooth cleaning element support. Such a channel may allow for fluid communication between an inner cavity of the toothbrush 100. The cavity, which may be bounded by the tooth cleaning element support and the head 104, will be discussed in more detail below.

In embodiments of this disclosure, the movable cleaning element 108 may be moved relative to the head by an actuator disposed in the head. The actuator may also be selected to provide an electrical field in the head 104. The electrical field may be useful to provide oral health benefits in addition to the benefits obtained by use of the tooth cleaning elements 110. The actuator may be controlled, at least in part, by a user operating the toothbrush 100. For example, a user interface 118, embodied as a power switch, is provided on the handle 102.

Figure 2:
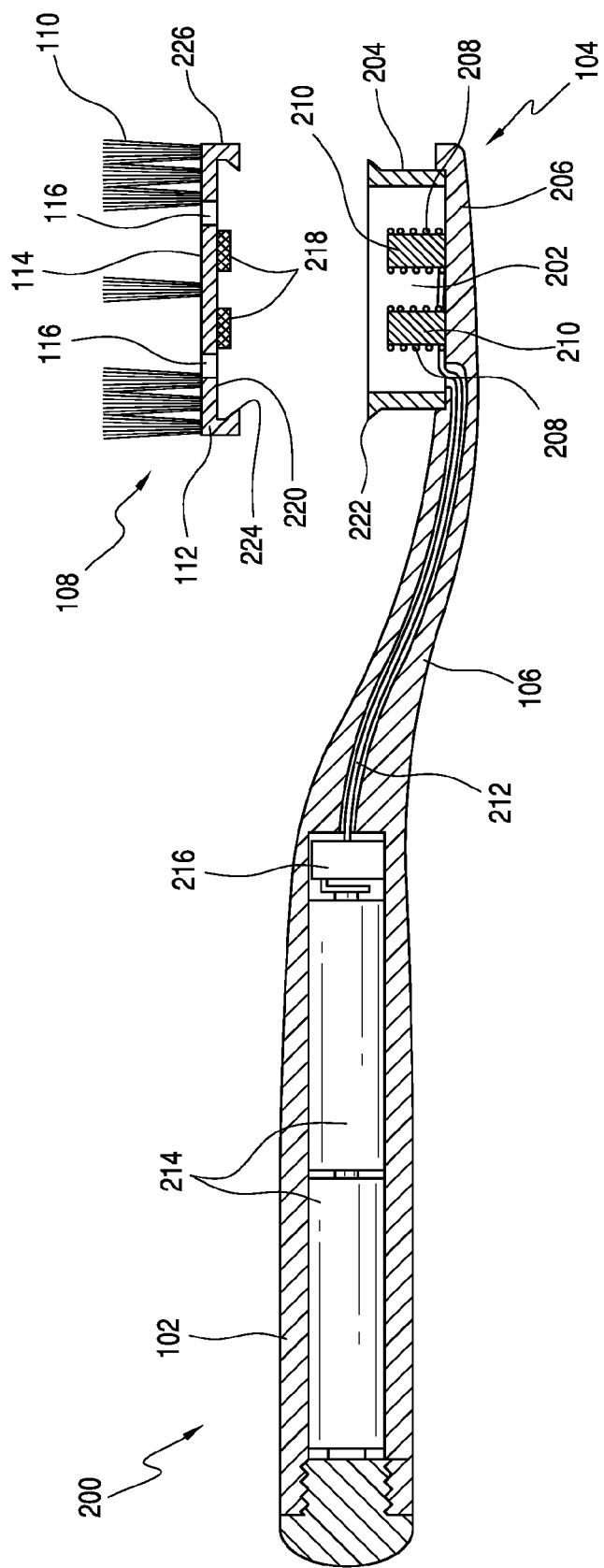
FIG. 2 is an exploded cross-sectional view of an example implementation of the toothbrush of FIG. 1, taken along section line A-A in FIG. 1.

FIG. 2 shows an exploded, cross-section of a toothbrush 200. The toothbrush 200 is an example implementation of the toothbrush 100. As illustrated, the head 104 of toothbrush 200 includes a cavity 202. The cavity 202 is a basin or void defined by a sidewall 204 that extends upwardly from a base 206 of the head 104. One or more (two are shown) electrically conducting elements 208 are disposed in the cavity 120. The electrically conducting elements may be any known shape or configuration, in addition to the configurations described in the examples herein. In some implementations, the electrically conducting elements 208 may be formed as electrical coils and include a number of turns of a metallic wire. In the illustrated embodiment each of the electrically conducting elements 208 includes such a winding, disposed about a core 210, which may be a ferrite core. Electrical or conductive leads 212 connect each of the electrodes 208 to a power source 214. In the illustrated embodiment, the power source 214 is a plurality of batteries disposed in the handle 102 and the leads 212 extend from the coils 208 through the neck 106 and into the handle 102 via a passageway or channel connected to the cavity 202 of the head 104. In some embodiments the batteries may be replaced with some other power source, and the power source may be rechargeable.

Application of current to the electrically conducting elements 208 creates an electrical field and a magnetic field generally along an axis of the electrodes 208 and, when present, the ferrite core 210. A controller and/or additional electronics 216 may also be provided. For example, the controller 216 may selectively allow current from the power source 214 to the electrically conducting elements 208. In some embodiments, the controller may alternate the current through the electrodes 208 and/or otherwise control the current, such as through pulse width modulation or alternating the current through the coils, to achieve desired activation sequences of the electrically conducting elements 208.

In FIG. 2, the movable cleaning element 108 also includes one or more (two are illustrated) ferromagnetic members 218 depending from a bottom surface 220 of the tooth cleaning element support 112, i.e., in a direction away from the tooth cleaning elements 110. The ferromagnetic members 218 may be permanent magnets, electromagnets, or any other material or structure that may be repelled and/or attracted by a magnetic field.

The movable cleaning element 108 is positioned relative to the head 104 to cover the cavity 202, and such that each of the ferromagnetic members 208 is arranged proximate one of the electrically conducting elements 208. In this example, selectively energizing the elements 208 will selectively attract or repel the counter magnets 116, resulting in movement of the movable cleaning element 108 relative to the remainder of the toothbrush 200. As should be appreciated, in the embodiment illustrated in FIG. 2, the counter magnets will generally move along an axis of the ferrite core, i.e., normal to the top surface 114 of the moveable element 108. In some embodiments, the controller may be programmed with one or more energizing sequences to effectuate one or more preferred vibrational patterns of the movable element 108. For example, current to the elements 208 may be alternated to alternately attract and repel the moveable cleaning element 108.

Although the movable cleaning element 108 is movable relative to the electrically conducting elements 208, the movable cleaning element 108 is retained on the head 104. Such retention preferably allows for the movable cleaning element 108 to move relative to the coils 208, without becoming detached from the head. For example, FIG. 2 shows a protuberance 222 at a distal end of the sidewall 204. Also, an inward projecting flange 224 is provided on the movable cleaning element 108, spaced from the bottom surface 220 of the tooth cleaning element support by a leg 226. In this embodiment, the movable cleaning element 108 is snapped onto the head 104 by passing the flange 224 downward over the protuberance 222. Once engaged, the protuberance 222 prevents ready removal of the movable cleaning element 108, but the movable cleaning element is capable of up-and-down movement. The movement is generally defined by a length of travel roughly approximate to a length of the leg 224 between the bottom surface 220 of the tooth cleaning element support 112 and the flange 224.

In the illustrated example, the up-and-down movement of the movable cleaning element 108 will result in an increase and decrease of the volume described above.

Structures that include mating features other than the protuberance 222 in the flange 224 will be appreciated by those with ordinary skill in the art having the benefit of this disclosure. Such alternative meeting features are within the scope of this disclosure.

Also in the embodiment of FIG. 2, the electrical conducting elements 208 may act as first and second electrodes, specifically, as an anode and a cathode. Controlling a current flowing between the first and second electrodes may be used to promote additional oral health benefits, to supplement the actions of the tooth cleaning elements 110. For example, the electrodes may interact with specific ingredients in a dentifrice slurry by converting relatively stable precursors in the dentifrice to active oxygen species and other therapeutic molecules. By way of non-limiting example, a slurry may be acted upon by the electrodes to generate oxidizing agents, such as $Cl_2$, $OCl^-$, and/or $HOCl$. In still other examples, the electrodes may be used to generate directly beneficial agents. For example, when one of the electrodes is made of zinc, selective energizing of the electrodes can generate different $Zn^{2+}$ species, which are effective anti-bacterial agents. In further examples still, the electrodes may be used to promote tooth-uptake of fluorine. The electrodes may also be used to suppress or mask breath or mouth malodor.

Thus, the electrical conducting elements 208 may act as both an electromagnets, e.g., to promote actuation, and electrodes, e.g., to produce an electro-chemical effect. More specifically, both a magnetic field and electrical field generated by the electrical conducting elements may be useful in embodiments of the disclosure. In other embodiments, the elements may promote only actuation or only the electrochemical effect. In still other embodiments, a plurality of electrodes may be provided that each performs one or more functions. In still another embodiment, it may be possible for the coil or surface to act as a catalyst without an applied electrical bias.

In some of the foregoing examples or other examples, particularly in embodiments where the electrical conducting elements 208 include electrodes, it may be desirable to allow for passage of fluids and the like from a position proximate the electrodes to a position in the oral cavity, such as in contact with a tooth. The apertures 116 may provide a flow path for this purpose. In one example embodiment, a slurry may be provided in the toothbrush, such as by being placed in the cavity 202 at the time of manufacture, that includes a relatively stable precursor, such as HCl acid. As the precursor is acted upon by the electrodes, $Cl_2$, an effective whitening agent, may be generated in the cavity 202. The $Cl_2$ may then exit the cavity 202, and enter the oral cavity, via the apertures 16. In some examples, flow may also be induced by changing the volume of the cavity 202. More specifically, a volume may be defined by the cavity 202 and the movable cleaning element 108, and movement of the moveable cleaning element 108 relative to the cavity 202 may expand or compress that volume. Increasing the volume will force result in fluid flow into the volume, whereas decreasing the volume with expel fluid from the volume. Of course, this is but one example, and others will be apparent to those having ordinary skill in the art, with the benefit of this disclosure.

Figure 3:
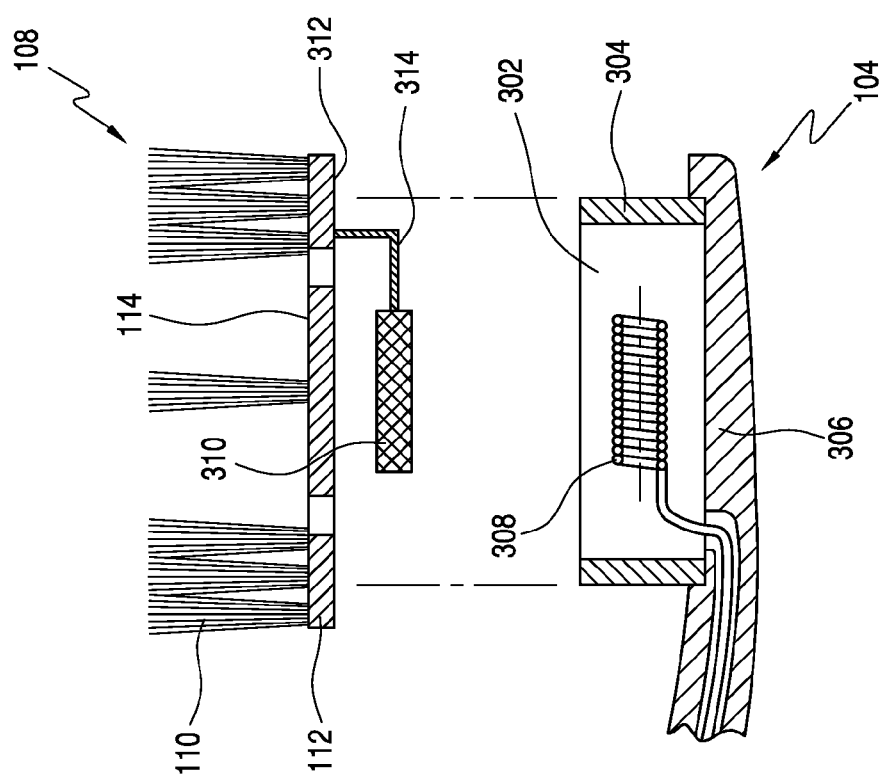
FIG. 3 is a partial, exploded cross-sectional view of another example implementation of a toothbrush of FIG. 1, taken along section line A-A in FIG. 1.

FIG. 3 illustrates a toothbrush 300 that is another example implementation of the toothbrush 100. The toothbrush 300 is similar to the toothbrush 200 in many respects. For example, as illustrated, the head 104 includes a cavity 302. The cavity 302 is a basin or void defined by a sidewall 304 extending upwardly from a base 306 of the head 104. Instead of two windings, however, the embodiment of FIG. 3 has only a single winding as an electrical conducting element 308. The winding 308 is arranged substantially normal relative to the elements 208 of the toothbrush 200, generally parallel to a longitudinal axis of the toothbrush 200.

In the embodiment of FIG. 3, the movable cleaning element 108 includes a ferromagnetic member 310 disposed below a bottom surface 312 of the tooth cleaning element support 112. In this embodiment, the ferromagnetic member 310 is fixed relative to the tooth cleaning element support 112, and is configured to be received within the winding 308. For example, in the illustrated embodiment, an arm 314 extends from the bottom surface 312 of the tooth cleaning element support 112, and is fixed to a distal end of the ferromagnetic member 310. In this arrangement, passing a current through the winding 308 will cause the ferromagnetic member 310, and thus the movable cleaning element 108, to move axially within the winding 308. As will be appreciated, like the embodiment illustrated in FIG. 2, the current can be controlled to create pre-determined vibratory sequences of the movable cleaning element 108. Also in the embodiment of FIG. 3, applying a current to the winding 308 may promote a chemical reaction, such as those discussed above.

Figure 4A:
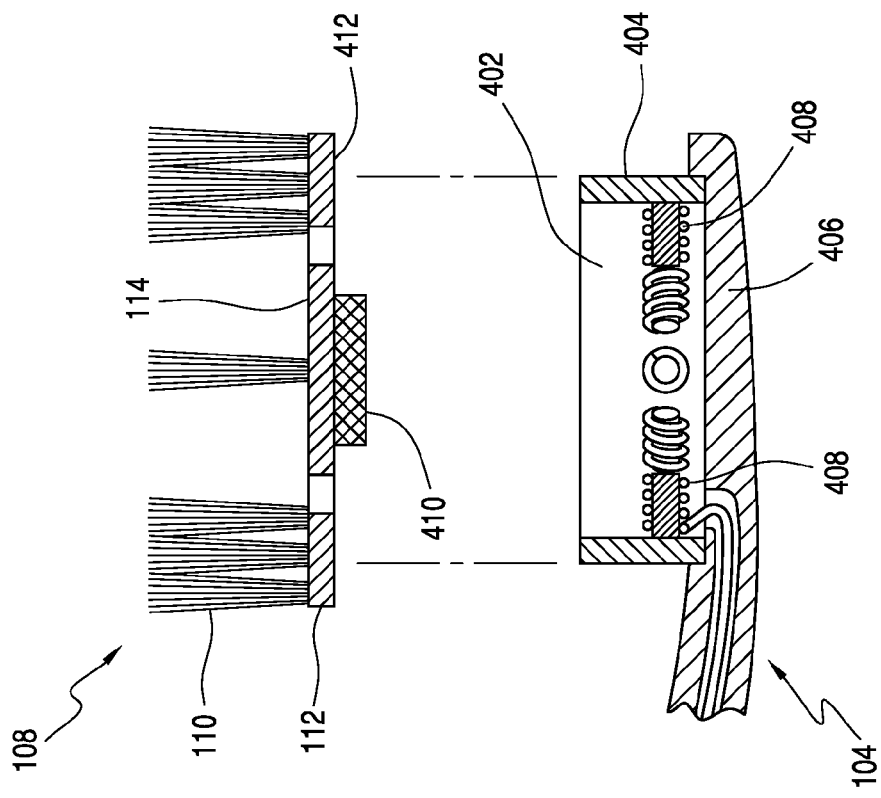
FIG. 4A is a partial, exploded cross-sectional view of an example implementation of the toothbrush of FIG. 1, taken along section line A-A in FIG. 1.

The embodiment of FIGS. 2 and 3 each provide for linear movement of the movable cleaning element 108. In each example, the movement is along a longitudinal axis of the respective winding comprising the electrically conducting elements 208, 308. FIG. 4A shows an alternative embodiment, which may provide a greater range of motion. FIGS. 4B-4F, described in more detail below, illustrate an example of this greater range of motion.

FIG. 4A illustrates a toothbrush 400, which is an alternative implementation of the toothbrush of FIG. 1. The head 104 of the toothbrush 400 includes a cavity 402. The cavity 402 is a basin or void defined by a sidewall 404 extending upwardly from a base 406 of the head 104. A plurality of electrical windings as electrically conducting elements 408 are disposed in the cavity 402, spaced about a periphery of the cavity 402. The movable cleaning element 108 includes a ferromagnetic member 410 extending from a bottom surface 412 of the tooth cleaning element support 112.

As with previously described examples, the windings act as electromagnets and electrical leads from a power source are disposed to selectively provide current to activate each of the windings 408. In use, the ferromagnetic member 410 may be attracted to or repelled by the activated winding(s) 408. By varying the order of activation, different motions of the tooth cleaning elements 110 may be achieved.

FIGS. 4B-4F provide a series of time-ordered schematic, top-view illustrations of depicting an example movement pattern, an elliptical motion, that may be achieved using the toothbrush 300. In FIGS. 4B-4F the windings 408 include eight windings 408*a*-408*h*. Those Figures also include a representation of the sidewall 404 and the ferromagnetic member 410. All other features have been removed for clarity.

In FIG. 3B, the winding 408*d* is activated, and the counter magnet is attracted to the winding 408*d*. Next, in FIG. 3C, the winding 408*d* is de-activated, and the windings 408*e*, 408*f* are activated. The ferromagnetic member 410 then moves toward the activating windings 408*e*, 408*f*, away from the now de-activated winding 408*d*. Similarly, in FIG. 3D, windings 408*e*, 408*f* are de-activated, while windings 408*g*, 408*h* are activated. Again, the ferromagnetic member 410 moves toward the activated windings 408*g*, 408*h* and away from the de-activated windings 408*e*, 408*f*. FIGS. 3E and 3F are similar, with windings 408*a*, 408*b* being activated in FIG. 3E and windings 408*c*, 408*d* being activated in FIG. 3F. Although motion of the ferromagnetic member 410 is discussed as resulting from an attraction to the activated winding, repulsion, or a combination of attraction and repulsion, may also be used.

The activation arrangement illustrated by FIGS. 4B-4H results in a clockwise rotation of the ferromagnetic member 410 (and thus of the tooth cleaning elements 110) among the spaced windings. This is but one example motion profile, however. As will be appreciated, the windings 408*a*-408*h* may be selectively activated in other profiles, to create any desirable cleaning pattern. By way of non-limiting example, the counter magnet 306 may be acted upon to move laterally, e.g., by alternately activating winding 408*b* (or windings 408*a*, 408*b*, 408*c*) and winding 408*f* (or windings 408*e*, 408*f*, 408*g*). In yet another embodiment, the windings 408*a*-408*h* may be selectively activated to effectuate an axial movement of the movable cleaning element 108 similar to the movement described above for the toothbrush 300, shown in FIG. 3. In this example, the wirings 408*d* and 408*h* may be alternately activated to effectuate a linear motion of the ferromagnetic member 410 between those windings.

Figure 5:
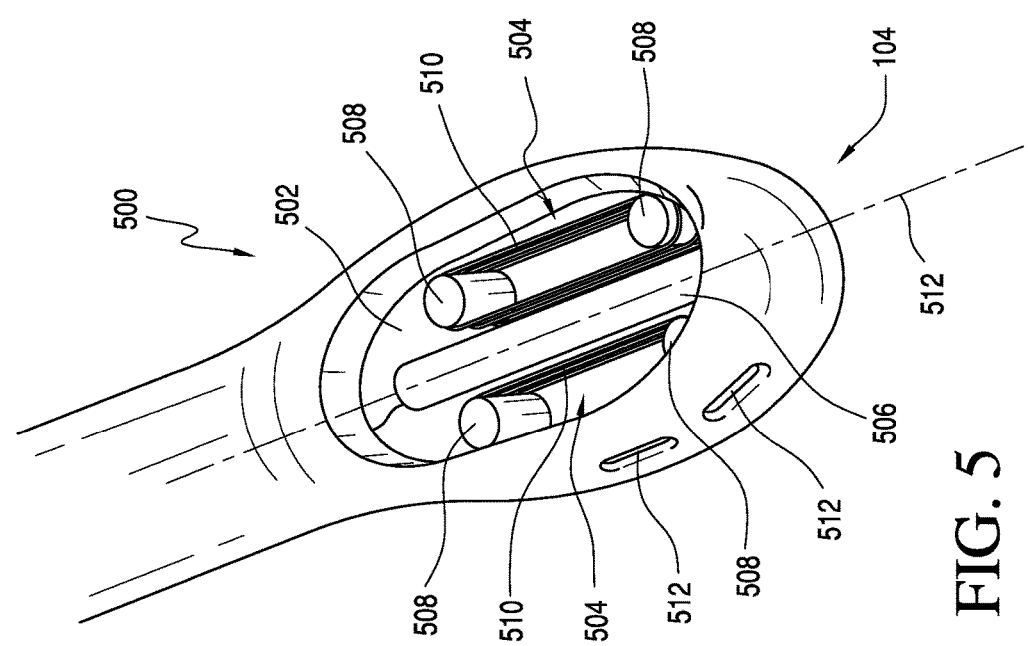
FIG. 5 is a perspective view of an oral care implement, embodied as a toothbrush, according to another example implementation of this disclosure.

FIG. 5 illustrates a toothbrush 500 according to another implementation of this disclosure. The toothbrush 500 includes a head 104 that defines a cavity 502, similar to the cavities discussed above. A pair of electrodes 504 and an actuator 506 are disposed in the cavity 502.

The electrodes 504 are disposed on either side of a longitudinal axis 512 extending generally along the handle of the toothbrush. Each of the electrodes 504 includes a pair of posts 508 spaced from each other and a wire 510 wrapped around the two posts 508. The wire 510 of each of the electrodes 504 is connected to a power source, which is controlled to selectively energize the electrodes 504, for example, to induce an electrochemical or chemical reaction in the head 104. In the example, two electrodes are shown in FIG. 5, each spaced from the other and defined by a wire 510 wrapped around the posts 508 on the respective side of the longitudinal axis 512 with portions of the wire 510 spanning between the posts 508 parallel to the longitudinal axis 512. In use, the two electrodes may act as an anode and a cathode. More or fewer electrodes may also be used. In other examples, each wire 510 may be wrapped about the posts 508 on respective sides of the longitudinal axis 512 in a woven or criss-cross fashion (not shown) such that portions of the wire 510 spanning between the posts 508 cross one another and extend non-parallel to the longitudinal axis 512. It is also contemplated, for example, that the electrodes 504 could be defined by wires 510 extending transversely between posts 508 on opposite sides of the longitudinal axis 512 (not shown).

The actuator 506 is positioned generally along, i.e., parallel to, the longitudinal axis 512. The actuator 506 includes a movable element, movable relative to the head 104, and the movement imparts a motion on the head 104. In this example, although not illustrated, the toothbrush 500 will also include a cleaning element 108 that is arranged to cover or otherwise close the cavity 502. Unlike in previous embodiments, however, where the cleaning element 108 moves relative to the head 104, in this example, the cleaning element 108 may be fixed to the head 104. The movement of the movable portion of the actuator imparts a movement on the entire toothbrush 500, including the head 104.

Although the cleaning element 108 may be disposed to occlude the cavity 502, a plurality of apertures 512 is also illustrated in FIG. 5. The apertures 512 may provide a passageway through which fluid or the like can be exchanged between the oral cavity and the cavity 502. In some implementations, a valve or the like (not illustrated) may be provided in the apertures to restrict or otherwise control flow between the cavity 502 and the oral cavity.

Figure 6A:
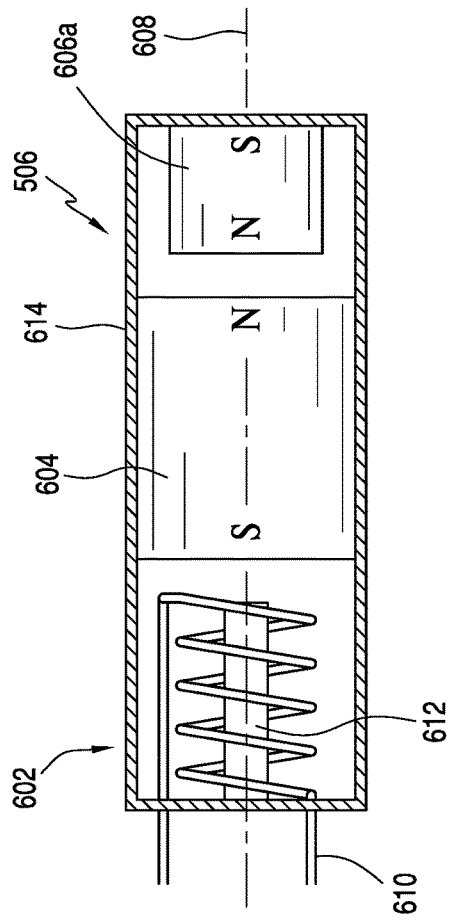
FIGS. 6A and 6B are schematic illustrations of driving devices usable in the oral care implement of FIG. 5.
Figure 6B:
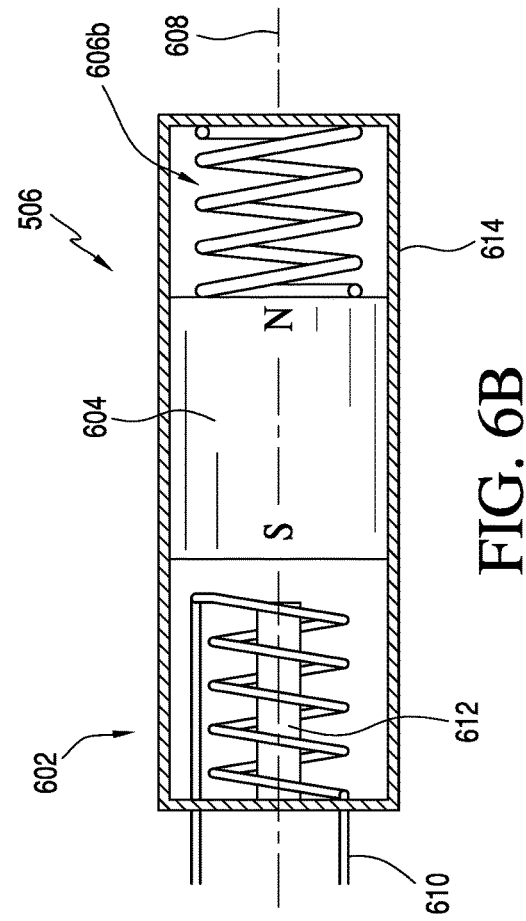

FIGS. 6A and 6B illustrate embodiments of the actuator 506. In those figures, the actuator 506 includes an electromagnet 602, a movable element 604 movable by the electromagnet 602, and a biasing member 606*a*, 606*b*. The actuator 506 is arranged generally along a longitudinal axis 608, e.g., such that the movable element moves along the axis 608. When incorporated in the toothbrush 500, the longitudinal axis 608 of the actuator 506 may be arranged substantially parallel to the axis 512 as in FIG. 5, although such is not required. In other implementations, the actuator may be arranged at an angle relative to the axis 512.

The electromagnet 602 includes a wire 610 disposed around a ferrite core 612. Selectively applying current to the wire 610 energizes the electromagnet 602 to form a magnetic field that may repel or attract the movable element 604. In the illustrations, the movable member 604 is a permanent magnet having a north pole and a south pole spaced along the longitudinal axis 608. In the embodiments shown in FIGS. 6A and 6B, the end of the electromagnet 602 proximate the movable member 604 may be a south pole when current is applied to the wire 610. Accordingly, energizing the coil will repel the moveable element 604 away from the electromagnet 602 and toward the biasing member 606a, 606b.

The biasing member 606a, 606b is disposed to bias the moveable element 604 toward the electromagnet 602. In FIG. 6A, the biasing member 606a is a stationary permanent magnet, having opposing north and south poles. When the north pole of the biasing member 606a is arranged proximate the north pole of the movable element 604, as in the figure, the movable element 604 repelled by the biasing member back to the electromagnet 602. FIG. 6B performs substantially the same function, e.g., to bias the moveable element 604 toward the electromagnet 602, but biasing member 606b is a spring, such as a coil spring. Other biasing members may also be used. For example, another electromagnet, such as the electromagnet 602 may be used as the biasing member. In still other embodiments, the biasing member may function more as a hard stop, with the field of the electromagnet being altered to attract the moveable member, back to the electromagnet.

In operation, the moveable element oscillates along the longitudinal axis 608. Energizing the electromagnet forces the movable element 604 toward the biasing member, and, in the examples of FIGS. 6A and 6B, the biasing member returns the movable element toward the electromagnet 602. The electromagnet 602, the movable element 604, and the biasing member 606a, 606b, may be retained in a housing 614. For example, the housing 614 may be configured to retain the components in appropriate alignment, and constrain the movement of the moveable element 604 between the electromagnet 602 and the biasing member 606. In this example, the housing 614 is fixed in the cavity 502, such as on a floor of the cavity. When the moveable element oscillates as described above, movement will be imparted on the entire toothbrush 500.

In the embodiment of FIG. 5, both the electromagnet 602 and the electrodes 504 are electrically conducting members. The actuator 506 is provided to impart a movement or vibratory effect on the toothbrush 500, whereas the electrodes 504 may be provided to promote a chemical or electrochemical response. For example, and as described above, the wires 510 of the electrodes 504 may be made of zinc, and applying a current the electrodes 504 may give off zinc ions. The electrodes 504 (as well as the electrodes discussed in other embodiments) may be formed from any suitable orally-acceptable metal or electrically conductive material, including for example but not limited to zinc, nickel, iron, stainless steel, and blends thereof, or other suitable materials, and are not limited to the wound coils illustrated in the Figures. In other embodiments, the electrodes may include flat electrodes, mesh electrodes, porous electrodes, and the like.

As noted above, different movement or vibration patterns may be desirable. For example, different vibration patterns, oscillation speeds, and durations of those patterns may be more effective at cleaning different portions of the oral cavity. Moreover, certain movement patterns may promote fluid flow between the cavity 202, 302, 402, 502 and the oral cavity, when such is desirable. Accordingly, for each of the embodiments described herein, it may desirable to program different motion profiles into a controller, such as the controller 216. For example, one or more profiles may correspond to one or more oral locations. In some embodiments, the controller may cycle through a plurality of the motion profiles based on a predetermined cleaning routine. A timer may also be used to start and/or stop different motion profiles.

In still other embodiments, the controller may receive a signal to commence (or end) a motion profile. The signal may be generated by the user, for example through interaction with a user input on the toothbrush, such as the input(s) 116. In still other embodiments, one or more sensors may be provided on the toothbrush to create the signal that selects a motion profile. Examples of such sensors may include a strain sensor located on the toothbrush, e.g., on the neck of the toothbrush, one or more positional sensors, or some other sensor that can aid in deducing a specific oral location.

Modifications to the foregoing embodiments are contemplated. For example, configurations and the number of coils used may be varied. Moreover, although not illustrated herein, in certain embodiments the head 104 may also include a soft tissue cleanser coupled to or positioned on its rear surface. An example of a suitable soft tissue cleanser that may be used with the present invention and positioned on the rear surface of the head 104 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of one or more ridges (elongated transverse, longitudinal, angled), nubs, or combinations thereof. Of course, the invention is not to be so limited and in certain embodiments the oral care implement 100 may not include any soft tissue cleanser.

Although example embodiments have been described in language specific to the structural features and/or methodological acts, the claims are not necessarily limited to the specific features or acts described. Rather, the specific features and acts are disclosed as illustrative forms of implementing the example embodiments.

What is claimed is:

1. A powered toothbrush comprising:
   a handle;
   a power source;
   a head including a cavity and disposed at a distal end of the handle, the cavity bounded by a floor and a peripheral side-wall completely surrounding the cavity, the cavity having an open top end defined by the peripheral side-wall;
   an electrically conducting element disposed in the cavity and electrically connected to the power source, wherein application of an electrical current from the power source to one or more of the electrically conducting elements generates a magnetic field; and
   a movable cleaning element connected to the head and covering the open top end of the cavity, the movable cleaning element movable relative to the cavity and comprising a bristle support member disposed at least partially over the cavity, a plurality of bristles extending from the bristle support member in a direction away from the cavity, and a ferromagnetic member;

wherein the magnetic field selectively at least one of attracts and repels the ferromagnetic member to move the movable cleaning element relative to the electrically conducting element.

2. The powered toothbrush of claim 1, wherein the electrically conducting element comprises an electrical winding disposed about a ferrite core.

3. The powered toothbrush of claim 1, wherein the electrically conducting element comprises an electrical coil and the ferromagnetic member is disposed in the electrical coil.

4. The powered toothbrush of claim 1, wherein the bristle support member and the cavity define a volume containing the ferromagnetic member.

5. The powered toothbrush of claim 4, further comprising a channel extending between the volume and an exterior of the head.

6. The powered toothbrush of claim 1, further comprising a dentifrice slurry in the cavity.

7. The powered toothbrush of claim 6, wherein the dentifrice slurry comprises one or more precursors converted by the electrically conducting elements to active species.

8. The powered toothbrush of claim 7, wherein the active species include at least one of a whitening agent, an enamel modifier, or an anti-bacterial.

9. The powered toothbrush of claim 1, wherein the ferromagnetic member is fixed to the cleaning element and the cleaning element is configured to move relative to the one or more electrically conducting elements.

10. The powered toothbrush of claim 1, further comprising a plurality of electrically conducting elements, wherein each of the plurality of electrically conducting elements is spaced about a periphery of the cavity.

11. The powered toothbrush of claim 1, wherein the ferromagnetic member is movable along a plane extending between magnetic fields of the plurality of electrically conducting elements.

12. The powered toothbrush of claim 11, further comprising a controller for selectively applying the current to individual of the electrically conducting elements.

* * * * *